United States Patent [19]

Müller et al.

[11] 4,332,645

[45] Jun. 1, 1982

[54] PROCESS FOR THE SEPARATION OF METHANOL FROM MIXTURES OF TETRAHYDROFURAN WITH METHANOL AND WATER

[75] Inventors: Wolfgang H. E. Müller; Michael Zölffel, both of Marl, Fed. Rep. of Germany

[73] Assignee: Chemische Werke Huls Aktiengesellschaft, Marl, Fed. Rep. of Germany

[21] Appl. No.: 167,443

[22] Filed: Jul. 10, 1980

[30] Foreign Application Priority Data

Jul. 11, 1979 [DE] Fed. Rep. of Germany ....... 2927931

[51] Int. Cl.³ .................... B01D 3/00; C07D 307/00
[52] U.S. Cl. ........................ 203/75; 203/14; 203/DIG. 19; 549/429
[58] Field of Search ............ 203/74, 75, 77, 81, 203/82, 14, DIG. 19, 99; 260/346.11; 568/916, 913

[56] References Cited

U.S. PATENT DOCUMENTS

| 3,219,547 | 11/1965 | Wheeler | 203/75 |
| 4,093,633 | 6/1978 | Tanabe et al. | 260/346.11 |
| 4,175,009 | 11/1979 | Copelin | 260/346.11 |

FOREIGN PATENT DOCUMENTS

| 1901870 | 11/1975 | Fed. Rep. of Germany . | |
| 50-24307 | 8/1975 | Japan | 260/346.11 |
| 52-48605 | 4/1977 | Japan | 260/346.11 |
| 53-39427 | 10/1978 | Japan | 203/77 |
| 549464 | 4/1977 | U.S.S.R. | 260/346.11 |

Primary Examiner—Wilbur L. Bascomb, Jr.
Attorney, Agent, or Firm—Craig and Antonelli

[57] ABSTRACT

A process for the continuous separation of methanol and water from a feed mixture containing predominantly tetrahydrofuran admixed with water, methanol and small amounts of additional compounds, in a rectifying apparatus having at last two rectifying columns, of which two are operated at different pressures which involves feeding the raw material into a first column operated under lower pressure, and introducing the distillate from the column operated under a lower pressure to a second column operated under a higher pressure, while a product stream from the second column operated under a higher pressure is reintroduced into the first column operated under a lower pressure. In this process the product stream withdrawn from the second column operated under a higher pressure is withdrawn as a side stream from the stripping or enrichment section of the second column and is returned into the first column operated under a lower pressure, while a methanol-enriched product stream containing practically all of the methanol introduced with the raw material into the rectifying apparatus is withdrawn from the head of the second column operated under a higher pressure. The first column is operated for example at atmospheric pressure and the second column is operated at a pressure of from 1 to 25 bar.

9 Claims, 1 Drawing Figure

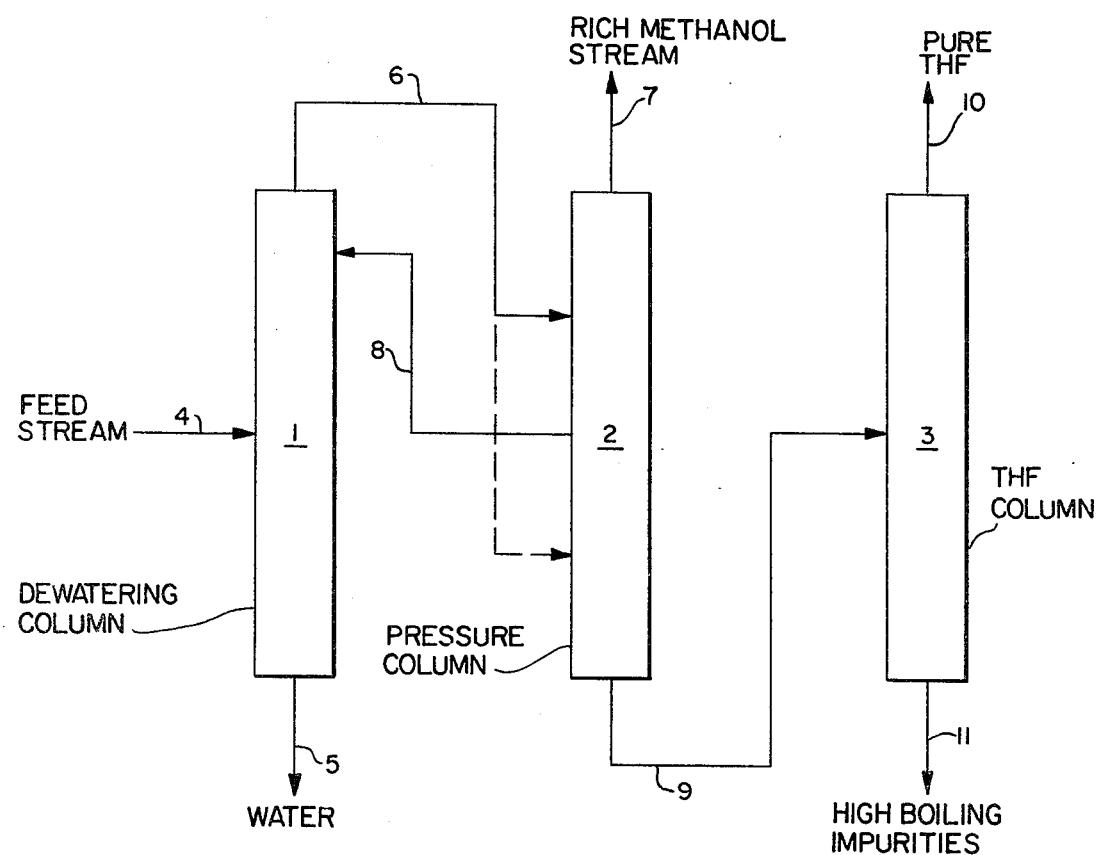

PROCESS FOR THE SEPARATION OF METHANOL FROM MIXTURES OF TETRAHYDROFURAN WITH METHANOL AND WATER

The invention relates to a process for the continuous separation of methanol from mixtures containing essentially tetrahydrofuran and, in addition, methanol, water, and in some cases additional substances.

The purpose of the invention is the obtaining of pure tetrahydrofuran which, in particular, does not contain any water or methanol, wherein for economical reasons only minor losses of tetrahydrofuran can be tolerated.

Tetrahydrofuran is manufactured, for example, from butanediol with sulfuric acid or acidic ion exchangers as the catalyst. The reaction products consist primarily of tetrahydrofuran and water, besides relatively small proportions of other materials, wherein also methanol can be present. As is known, water is completely miscible with tetrahydrofuran and, in addition, these compounds form a minimum azeotrope. Therefore, for the drying of tetrahydrofuran, the method normally utilized for dewatering organic liquids forming minimum azeotropes with water, namely rectification in two columns wherein the head products of both columns have an azeotropic composition and, after condensation in a separating flask, are separated into two liquid phases, is not suitable because the minimum azeotrope does not separate into two liquid phases. This difficulty was overcome conventionally by bringing about a separation into two liquid phases by adding a third component, and thereafter rectifying the thus-separated liquid phases. Furthermore, processes used for the separation of water and tetrahydrofuran are extractive distillation, absorption processes, or methods based on a chemical reaction. A particularly noteworthy method for dewatering tetrahydrofuran is the rectification in two columns operated at different pressures, wherein the head products of one column are reintroduced, respectively, into the other column, and the separated compounds, water and tetrahydrofuran, are withdrawn from the column sumps (DAS [German Published Application] No. 1,901,870). All of these processes lead to difficulties, if more than about 0.01% of methanol is contained in the aqueous tetrahydrofuran to be worked up. Heretofore, no methods have become known, by means of which methanol-containing tetrahydrofuran can be freed from water and methanol and isolated in high yields and high purity. Such methanol-containing, crude tetrahydrofuran products are formed when using, for example, in place of the relatively expensive pure 1,4-butanediol, the impure 1,4-butanediol coming from the polyester manufacture as a raw material for the synthesis of tetrahydrofuran with sulfuric acid as the catalyst.

There is thus the problem of finding a method permitting the separation of methanol from such mixtures containing tetrahydrofuran, water, methanol and in some cases additional substances, and the production, in maximally high yields, of pure tetrahydrofuran, i.e. one which corresponds to the usual commercial qualities, which tetrahydrofuran is practically free of methanol and water. The source where this methanol containing mixture comes from is optional.

The solution of this problem according to the invention has been found by rectifying the methanol-containing, moist tetrahydrofuran in a system of at least two columns without adding any further substances, namely in such a way that the two columns are operated under different pressures, the distillate from the column operated under lower pressure being fed to the column operated under higher pressure, and a side stream is withdrawn from the stripping or enrichment section of the column operated under higher pressure, this side stream being returned into the column operated under lower pressure. At the head of the column operated under higher pressure, a methanol-rich water-depleted product is withdrawn which contains practically all of the methanol introduced with the raw material into the rectification apparatus. Tetrahydrofuran-free water is obtained in the sump of the column operated under lower pressure, and anhydrous and methanol-free tetrahydrofuran is obtained in the sump of the column operated under higher pressure. The water- and methanol-free tetrahydrofuran can—if necessary—be freed conventionally of higher-boiling impurities, such as, for example, methyltetrahydrofuran, in a third rectifying column.

The accompanying schematic drawing has a single FIGURE of the arrangement of columns required for carrying out the process of this invention. In this drawing all those devices have been omitted which are not specific for the present invention and which are well known to the experts.

In this FIGURE, the feed stream 4 of material, which can contain, besides tetrahydrofuran, water, and methanol, also other compounds, such as, for example, 1,4-butanediol or 3-methyltetrahydrofuran, is introduced into a continuously operated rectifying column 1. Such mixtures are obtained, for example, in the synthesis of tetrahydrofuran from 1,4-butanediol with acidic catalysts, particularly if raw materials are employed containing, in addition to 1,4-butanediol, still other substances (e.g. methyl esters). The rectifying column 1 is a column of the customary type of construction, i.e., for example a bubble cap column, a valve tray column, or a packed column operated under a pressure which is markedly lower than the pressure in column 2; the pressure in column 1 can be normal pressure, i.e. atmospheric pressure. Depending on the concentration of the stream 4 of material, it is advantageous to provide 10-30 theoretical separating stages and reflux ratios of between 0.5 and 20. The water contained in the raw material is withdrawn—practically free of tetrahydrofuran—from the sump of column 1 (product stream 5). This stream 5 can also contain still other compounds which may be present in the raw material, such as, for example, 1,4-butanediol. With the overhead product stream 6 of compounds, the column 2 is supplied with the entire amount of tetrahydrofuran fed to column 1, with the entire amount of methanol fed to column 1, with part of the water fed to column 1, and perhaps still additional compounds present, such as, for example, 3-methyltetrahydrofuran. Column 2 is always operated under a higher pressure than column 1 (for example under a pressure of between 1 and 25 bar, preferably between 10 and 15 bar). Stream 6 can be fed into column 2 above the side stream withdrawal point, as well as below the side stream withdrawal point, as shown by dash line 6. Column 2 is a packed column of the usual type of construction, e.g. a column filled with Pall rings or Raschig rings measuring 25 mm in diameter, and should exhibit about 15-50 theoretical stages. From the head of column 2, the entire methanol fed with feed stream 4 is discharged in the form of a methanol-enriched substance overhead stream 7 low in water. A side stream 8 is taken either from the enrichment or stripping section of the column, in the vapor or liquid phase, containing practically the entire amount of water introduced with stream 6 into column 2 and is reintroduced into the middle part of column 1. Below the point where side stream 8 is taken column 2 has a length being long enough for the separation of a mixture of tetrahydrofuran and water without any methanol, that means this lower part of column 2 contains between 10 and 30 theoretical stages. Above that point column 2 contains further 5-30 theoretical stages. The product stream 9 is withdrawn from the sump at the bottom of column 2, containing, except for the minor amount of tetrahydrofuran contained in the stream 7, practically the entire quantity of tetrahydrofuran fed to the separating plant within the feed stream 4. This product stream 9 can, insofar as this is necessary, be separated in a column 3 into an especially pure tetrahydrofuran (as overhead product stream 10) and into a practically tetrahydrofuran-free product stream 11 containing compounds boiling higher than tetrahydrofuran, such as, for example, 3-methyltetrahydrofuran. The column 3 has, for example, 15-40 theoretical stages and is operated at reflux ratios of between 0.5 and 20.

The product streams 5, 7 and 11 can be worked up to recover other compounds contained therein, or they are discarded in an ecologically harmless fashion. The methanol-rich stream 7 can also be utilized as a solvent.

In the initial feed stream 4 the water content has to be at least 1%, preferably 5% by weight or more, based on the amount of tetrahydrofuran in stream 4. There is no upper limit of the water content. The methanol content in stream 4 has to be between zero and about 100% by weight, preferably between zero and 5% by weight, based on the amount of tetrahydrofuran in stream 4. The content of high boiling compounds in stream 4 is optional.

If the water content in stream 4 is below 1% by weight based on the amount of tetrahydrofuran in stream 4 or below 5% by weight at high operating pressure in column 1 an adequate amount of water may be added to stream 4 or stream 4 is fed to column 2 instead of column 1.

The advantages of the process of this invention reside in that it is possible to work up even methanol-containing raw tetrahydrofuran in high yields into especially pure tetrahydrofuran, and that this can be accomplished without any additional apparatus expensive in initial investment and in operation. The only additional expenditure necessary is the lengthening of the dehydrating zone, operated in a conventional way, in the column 2 which operates under higher pressure. Column 2 used in this invention is longer than a column necessary for the separation of a mixture of tetrahydrofuran and water without any methanol. The apportionment of the total length of column 2 to the enrichment zone, the stripping zone and the medium zone between the inlet conduit of stream 6 and the outlet conduit of stream 8 depends on the methanol content of stream 6. There is no need for providing additional energy, since evaporation in the sump of the column operated under higher pressure must be conducted anyway. Without the lengthening of the column operated under a higher pressure and the withdrawal of a methanol-enriched product from the head of this column, methanol would collect within a short period of time at the upper ends of the two dehydrating columns when processing a methanol-containing raw tetrahydrofuran, and no additional water would be separated any longer.

The general operating conditions of the process according to the invention have the following suitable ranges:

| Column No. | Absolute pressure | Temperature | Reflux ratio |
|---|---|---|---|
| 1 | 0.1-3 bar | 0-130° C. | 0.5-20 |
| 2 | 1-25 bar but always higher than pressure in column 1 | 55-240° C. | 10-300 at very small portions of methanol in stream 4 a suitable higher reflux ratio |
| 3 | 0.5-5 bar | 45-150° C. | 0.5-20 |

The process of this invention represents a substantial improvement of the state of the art, inasmuch as it is now possible to convert even other raw materials, substantially less expensive than pure 1,4-butanediol, into tetrahydrofuran in high yields, and to separate tetrahydrofuran free of water and methanol from mixtures of other sources containing these components by rectification only, without having to tolerate any other disadvantages as a consequence. In addition to the technical advantage, this represents an essential economical advantage.

The process of this invention will be explained with the aid of the examples set forth below.

EXAMPLE 1

A mixture of 24.1% by weight of water, 1.95% by weight of methanol, and 73.95% by weight of tetrahydrofuran was continuously rectified in two rectifying columns (columns 1 and 2) as shown in the accompanying drawing. The first column had 30 practical plates; the aforementioned raw material was introduced in the liquid phase at boiling temperature, i.e. 85° C. to the sixth plate from the bottom, and the side stream withdrawn from the second rectifying column was fed to the seventh plate from the bottom. The first column was operated under normal pressure with a reflux ratio of one. The second column was a packed column of 4 meters packed height, operated under a pressure of 10 bar (absolute), likewise at a reflux ratio of one. The distillate of the first column was introduced at a packing height of 1.5 m, while the side stream was withdrawn in the liquid phase at a height of 2.5 m. In this connection, one-half of the liquid flowing through the column was withdrawn at this point. From the head of the second column with a reflux ratio of 70, 2.7% by weight (based on the raw material introduced into column 1) of a product with 0.02% by weight of tetrahydrofuran, 70.6% by weight of methanol and 29.4% by weight of tetrahydrofuran was discharged. While there was obtained in the sump of the second column 73.2% by weight (based on the raw material fed to column 1) containing >99.9% by weight of tetrahydrofuran and water and methanol contents of respectively below 0.05% by weight, the product withdrawn from the sump of the first column was 24.1% by weight (based on the raw material fed to column 1), containing less than 0.05% by weight of tetrahydrofuran.

If all partial amounts are based on the amount of raw material employed, the following results:

| Stream No. | Partial Amounts Based on Raw Material Quantity = 100% by Weight | | | |
|---|---|---|---|---|
| | Tetrahydro-furan | Methanol | Water | Sum Total |
| 4 | 73.95 | 1.95 | 24.1 | 100 |
| 5 | <0.01 | <0.02 | 24.07 | 24.1 |
| 7 | 0.80 | 1.90 | 0.001 | 2.7 |
| 9 | >73.14 | <0.03 | <0.03 | 73.2 |

In this example, the temperatures in the columns are:

| | Column 1 | Column 2 |
|---|---|---|
| Head | 64° C. | 137° C. |
| Sump | 101° C. | 162° C. |

EXAMPLE 2

In an apparatus consisting of three rectifying columns (columns 1, 2 and 3), a raw tetrahydrofuran was continuously rectified having the following composition:
26.3% by weight of water
0.83% by weight of methanol
71.0% by weight of tetrahydrofuran
1.87% by weight of other substances
obtained from a so-called unreacted 1,4-butanediol from the polyester manufacture. The first column had 30 practical plates, the raw material was fed in the liquid phase at boiling temperature, i.e. 85° C., to the sixth plate from the bottom, the side stream was returned from column 2 to the seventh plate from the bottom. The column was operated under normal pressure with a reflux ratio of one.

The second column was a packed column with 4 meters of packing, wherein the distillate of the first column was fed at a packing height of 3 meters to the second column. The side stream was withdrawn at a packing height of 2.5 m, wherein one-half of the liquid flowing through the column at this height was withdrawn as a side stream and reintroduced into the first rectifying column. From the head of the column, a methanol-enriched distillate was removed with a reflux ratio of 80. The sump product of this second rectifying column was fed to a third rectifying column operated under normal pressure and having in total 45 practical plates, at the 25th plate from the bottom. This third rectifying column was operated at a reflux ratio of 3. Based on the raw material introduced into the first column, the following quantities were obtained:
26.9% sump, column 1
1.35% distillate, column 2
70.6% distillate, column 3
1.15% sump, column 3
The sump product from the first column was water with relatively small portions of other compounds. The tetrahydrofuran content was <0.05% by weight.

The distillate from the second column contained 61.2% by weight of methanol, 0.8% by weight of water, 33.9% by weight of tetrahydrofuran, and relatively small quantities of other compounds.

The distillate from the third column was tetrahydrofuran with a content of >99.9% by weight.

The sump product from the third column was constituted by higher-boiling compounds. The tetrahydrofuran content was <0.05% by weight.

If all partial quantities are based on the amount of raw material employed, the following results are obtained:

| Stream No. | Partial Amounts Based on Raw Material Quantity = 100% by Weight | | | | |
|---|---|---|---|---|---|
| | Tetrahydro-furan | Methanol | Water | Other Compounds | Sum Total |
| 4 | 71.0 | 0.83 | 26.3 | 1.87 | 100 |
| 5 | <0.01 | <0.01 | 26.24 | 0.64 | 26.9 |
| 7 | 0.48 | 0.80 | 0.02 | 0.05 | 1.35 |
| 10 | >70.5 | <0.01 | <0.04 | <0.04 | 70.6 |
| 11 | <0.001 | <0.001 | <0.001 | >1.14 | 1.15 |

The pressure in column 2 is 10 bar absolute. The temperatures are:

| | Column 1 | Column 2 | Column 3 |
|---|---|---|---|
| Head | 64° C. | 137° C. | 67° C. |
| Sump | 101° C. | 162° C. | 117° C. |

What is claimed is:

1. A process for the continuous separation of methanol from a feed mixture containing tetrahydrofuran, water and methanol in a rectifying apparatus having at least two rectifying columns, of which two are operated at different pressures, which comprises introducing the feed mixture into a first rectifying column operated under a lower pressure than a second rectifying column, feeding distillate containing a water/tetrahydrofuran azeotrope from the first column into the second column, withdrawing a product stream rich in water from the second column operated at a higher pressure as a side stream and introducing said side product stream into said first column, withdrawing a methanol enriched product stream containing substantially all of the methanol introduced with the feed mixture from the head of the second column and from the apparatus, and withdrawing a sump product containing substantially dry tetrahydrofuran from the second column.

2. A process according to claim 1, wherein the first column is operated under about atmospheric pressure and the second column is operated under a pressure of between 1 and 25 bar, the pressure in the second column always being higher than the pressure in the first column.

3. A process according to claim 1 or claim 2, wherein the feed mixture contains a raw tetrahydrofuran which was obtained by an acid-catalyzed reaction from impure 1,4-butanediol.

4. A process according to claim 1, wherein said feed mixture further contains higher boiling point impurities and said process comprises withdrawing a sump product stream containing substantially dry tetrahydrofuran and the higher boiling point impurities from the second column and then introducing the sump product stream into a third rectifying column, withdrawing pure tetrahydrofuran from the head of the third column and withdrawing a sump product from the third column containing said higher boiling point impurities.

5. A process according to claim 1, wherein the product stream rich in water withdrawn from the second column as a side stream is taken from a stripping section of the second column.

6. A process according to claim 1, wherein the product stream rich in water withdrawn from the second column as a side stream is taken from an enrichment section of the second column.

7. A process according to claim 1, wherein the distillate from the first column is introduced into the second column above the section of the second column from which the side product stream is withdrawn from the second column.

8. A process according to claim 1, wherein the distillate from the first column is introduced into the second column below the section of the second column from which the side product stream is withdrawn from the second column.

9. A process according to claim 1, further comprising withdrawing a sump product stream containing water substantially free of tetrahydrofuran from the first column and from the apparatus.

* * * * *